United States Patent [19]

Louis et al.

[11] Patent Number: 5,242,943
[45] Date of Patent: * Sep. 7, 1993

[54] 3-AMINOPROPOXYPHENYL DERIVATIVES, THEIR PREPARATION AND PHARMACEUTICAL COMPOSITIONS CONTAINING THEM

[75] Inventors: William J. Louis, 5 Von Nida Crescent, Rosanna, Victoria, Australia; Max-Peter Seiler, Riehen; Andre Stoll, Birsfelden, both of Switzerland

[73] Assignee: William J. Louis, Victoria, Australia

[*] Notice: The portion of the term of this patent subsequent to Sep. 24, 2008 has been disclaimed.

[21] Appl. No.: 738,014

[22] Filed: Jul. 30, 1991

Related U.S. Application Data

[63] Continuation of Ser. No. 536,055, Jun. 11, 1990, Pat. No. 5,051,445, which is a continuation of Ser. No. 294,961, Jan. 9, 1989, abandoned, which is a continuation of Ser. No. 807,068, Nov. 21, 1985, abandoned.

[30] Foreign Application Priority Data

Mar. 28, 1984 [CH] Switzerland ............ 1554/84
Mar. 28, 1984 [CH] Switzerland ............ 1555/84

[51] Int. Cl.$^5$ .................................... A61K 31/35
[52] U.S. Cl. ............................................ 514/459
[58] Field of Search ..................... 549/425; 514/459

[56] References Cited

U.S. PATENT DOCUMENTS 4,661,513 4/1987 Berthold et al. ............... 549/425

Primary Examiner—Nicky Chan
Attorney, Agent, or Firm—Sughrue, Mion, Zinn, Macpeak & Seas

[57] ABSTRACT

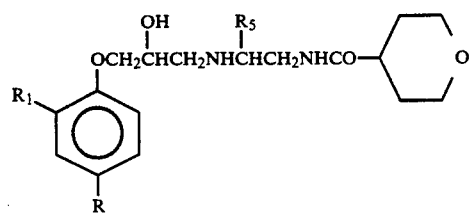

The compounds of Formula I and their physiologically hydrolysable derivatives, in which at least one hydroxy group is in esterified form, and their salts, elicit highly cardioselective beta 1 adrenoceptor blockade, and in most cases cardiospecific blockade, and relevant cardiotonic activity. These compounds can be used as therapeutic agents. One obtains these compounds by 3-amino-2-oxypropylation of the respective substituted phenol.

6 Claims, No Drawings

3-AMINOPROPOXYPHENYL DERIVATIVES, THEIR PREPARATION AND PHARMACEUTICAL COMPOSITIONS CONTAINING THEM

This is a continuation of application Ser. No. 07/536,055, filed Jun. 11, 1990, now U.S. Pat. No. 5,051,445, which is a continuation of application Ser. No. 07/294,961, filed Jan. 9, 1989, abandoned, which is a continuation of application Ser. No. 06/807,068, filed Nov. 21, 1985, abandoned.

The present invention relates to compounds of Formula I,

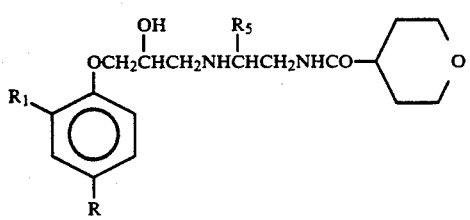

wherein
A) R is O(CH$_2$)$_2$O—R$_3$ and
  (a) R$_1$ and R$_5$ are hydrogen and R$_3$ is n-propyl, isobutyl, cyclopentylmethyl, benzyl or 2-(p-fluorophenyl)ethyl;
  (b) R$_1$ is fluorine and R$_5$ is hydrogen and R$_3$ is n-propyl;
  (c) R$_1$ is methyl and R$_5$ is hydrogen and R$_3$ is cyclopropylmethyl;
  (d) R$_1$ is cyano and R$_5$ is hydrogen and R$_3$ is n-propyl;
  (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen,
and their physiologically hydrolysable derivatives, in which at least one hydroxy group is in esterified form.

Physiologically hydrolysable derivatives are derivatives, in which under physiological conditions the esterified hydroxy groups are de-esterified to give the corresponding hydroxy compound.

An example of an esterified compound is shown as Formula E.

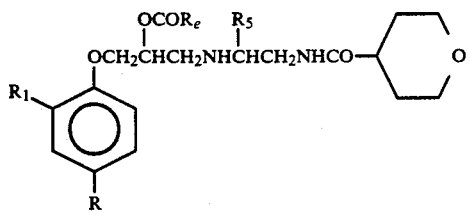

wherein R, R$_1$ and R$_5$ are as defined above and R$_e$ is alkyl with 1 to 12 carbon atoms, cycloalkyl with 3 to 7 carbon atoms, or phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

Preferred are compounds in which a hydroxy group is not esterified.

In accordance with the invention the compound of the invention may be obtained by a process which includes the step of appropriately 3-amino-2-oxypropylating a corresponding compound of Formula II,

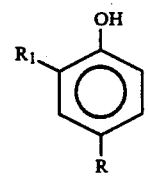

wherein R and R$_1$ are as defined above or a precursor form thereof.

The process step of the invention may be effected in conventional manner for the production of analogous 3-amino-2-oxypropoxyaryl compounds.

The choice of the most appropriate variants should, of course, take into account the reactivities of the substituents present.

A precursor form of the compound of Formula II is a compound capable of being converted into a compound of Formula II, e.g. by appropriate etherification, aromatic substitution and/or deprotection.

When R is —OCH$_2$CH$_2$O—R$_3$, a precursor form is for example a corresponding compound wherein the moiety —OCH$_2$CH$_2$O—R$_3$ is replaced by a hydroxy group, in optionally protected form.

Benzyl, methyl or 2-tetrahydropyranyl, preferably benzyl, are examples of a protecting group on for example a hydroxy substituted phenyl ring.

Thus, the process step of invention may be effected in more than one stage. For example, a compound of Formula II in protected form may be used, or a 3-amino-3-oxypropyl moiety in protected form may be introduced, and subsequently, after 3-amino-2-oxypropylation has been effected, the protecting group present may be split off.

In one form of the process according to the invention, the 3-amino-2-oxypropylation is effected in two main process stages.

In the first process stage a group CH$_2$R$_x$ wherein R$_x$ is a group capable of reacting with a primary amine to give a 2-amino-1-hydroxy ethyl group is introduced by O-alkylation in the one position into a compound of Formula II to give a corresponding compound of Formula III.

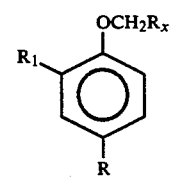

wherein R$_1$ and R$_x$ are as defined above.

In the second process stage a compound of Formula III is aminated with a corresponding compound of Formula IV,

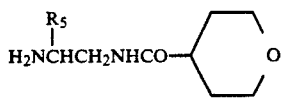
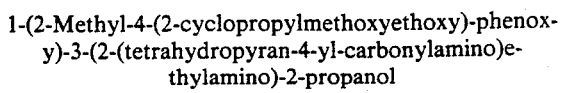

wherein $R_5$ is hydrogen or methyl, and where required at least one hydroxy group in a resulting compound of Formula I is appropriately esterified.

The O-alkylation process stage in the one position may be effected in a manner known for the production of analogous ethers. A compound of Formula II preferably is reacted in an ionic form.

The amination process stage may be effected in conventional manner for the production of analogous 3-amino-2-hydroxypropoxyaryl compounds. For example, $R_x$ may be a group of

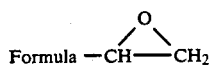

or a derivative of this group for example a group of Formula —CH(OH)CH$_2$—L wherein L is chlorine, bromine or a group $R_ySO_2O$— wherein $R_y$ is phenyl, tolyl or alkyl. L is preferably chlorine. The reaction is preferably effected in ethanol or in an appropriate ether such as dioxane. Optionally an excess of the amine may be used as solvent. Alternatively the reaction may be effected in a fusion melt. Suitable reaction temperatures may be from about 20° to about 200°. Conveniently the reflux temperature of the reaction mixture if a solvent is used.

The optional esterification in a resultant compound of Formula I may be effected in a manner known for the production of analogous esters, if necessary, using selective conditions when other reactive groups, for example hydroxy or amino are present.

The compounds of the invention may exist in free form, i.e. normally as a base, or in salt form. Free forms of the compounds of the invention may be converted into salt forms, for example acid addition salt forms, and vice versa, in a conventional manner. Suitable acids for acid addition salt formation include hydrochloric, malonic, succinic, oxalic and fumaric acid.

In the compounds of the invention the carbon atom in for example the 2 position of the 3-amino-propoxy side chain is asymmetrically substituted and when $R_5$ is methyl the carbon atom on the alkylene side chain is also asymmetrically substituted. The compounds may thus exist in the racemate form or individual optical isomer forms. The preferred optical isomer has the S-configuration at the asymmetrically substituted carbon atom of the 3-amino-propoxy side chain and when $R_5$ is methyl on the alkylene side chain the preferred conformation has the R-configuration. Individual optical isomer forms may be obtained in conventional manner, for example by using optically active starting materials or by fractional crystallization of racemate salts using optically active acids.

In so far as the preparation of any particular starting materials is not particularly described, this may be effected in conventional manner. In the following examples all temperatures are in degrees centrigrade and are uncorrected.

EXAMPLE 1

1-(2-Methyl-4-(2-cyclopropylmethoxyethoxy)-phenoxy)-3-(2-(tetrahydropyran-4-yl-carbonylamino)ethylamino)-2-propanol 3.0 g of 4-(2-(cyclopropylmethoxy)ethoxy)-1-(2,3-epoxypropoxy)-2-methylbenzene is refluxed with 2.3 g of N-(2-amino-ethyl)tetrahydropyran-4-carboxamide (obtained by reacting tetrahydropyran-4-carboxylic acid ethyl ester with ethylenediamine) in 100 ml methanol for three hours, with stirring. The resultant oil is chromatographed over silica gel with methylene chloride/ethanol/conc. ammonia (150:27:3). Late eluting fractions containing the title compound is taken up in ethylacetate and 2M NaOH solution and washed with water. The organic phase is dried over magnesium sulfate and following removal of solvent the title compound is recrystallized from methanol/ether (M.P. 80°–83°).

The epoxide starting material is obtained from reaction of 4-hydroxy-3-methylphenyl benzoate with benzyl bromide to give 4-benzyloxy-3-methylphenyl benzoate (M.P. 120°–121° from methanol/ether), followed by de-esterification with 2M NaOH solution to give 4-benzyloxy-3-methylphenol (M.P. 69°–70° from ether/hexane) and reaction with 2-bromoethanol (light brown oil) to form an alcohol which is reacted with cyclopropylmethyl bromide in tetrahydrofuran. Debenzylation of the cyclopropylmethoxyethoxy derivative (unpurified) with 10% Pd on activated charcoal forms 4-(2-(cyclopropylmethoxy)ethoxy)-2-methylphenol which is then reacted with epichlorhydrin in the presence of a catalytic amount of piperidine to give 2-methyl-1-(2,3-epoxypropoxy)-4-(2-(cyclopropylmethoxy)ethoxy)benzene (light brown oil after chromatography on silica gel with toluene/ethyl-acetate (8:2)).

EXAMPLE 2

1-(2-fluoro-4-(2-propoxy-ethoxy)phenoxy)-3-(2-(tetrahydropyran-4-yl-carbonylamino)ethylamino)-2-propanol Method A: N-(2-aminoethyl)-tetrahydropyran-4-carboxamide is reacted with 1-(2,3-epoxypropoxy)-2-fluoro-4-(2-propoxyethoxy)benzene giving the title compound (melting point 107°–108°—from ethyl acetate).

The epoxide starting material is obtained by reacting 3-fluoro-4-methoxyphenol with 1-bromo-2-propoxyethane. After work up of the reaction mixture 2-fluoro-1-methoxy-4-(2-propoxyethoxy)benzene is obtained which is then reacted with sodium thioethoxide giving 2-fluoro-4-(2-propoxyethoxy)phenol which is then reacted with epichlorhydrin in the presence of a catalytic amount of piperidine.

Method B: 2.1 gm of 1-(2-fluoro-4-hydroxyphenoxy)-3-(2-(tetrahydropyran-4-yl-carbonyl-amino)ethylamino)-2-propanol is reacted with 0.15 gm of sodium hydride in dimethylformamide at room temperature. After 30 minutes stirring at room temperature 1.5 gm of 2-bromoethyl propylether in dimethylformamide is gradually added and maintained at 100° for 16 hours. Excess sodium hydride is removed with methanol and the mixture evaporated. The residue is extracted with methylene chloride and water, and the organic layer chromatographed over silica gel with methylene chloride/ethanol/ammonia 35% in water (90:9:1). The title compound is obtained (M.P. 107°–108° from ethyl acetate).

From the appropriate compounds of Formula III wherein $R_x$ is

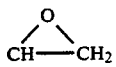

and the appropriate compound of Formula IV the examples numbered 3 to 8 of Formula I are obtained in analogous manner to examples 1 and 2.

| Example No. | $R_1$ | $R_5$ | R | M.P. (as base) |
|---|---|---|---|---|
| 3 | H | H | O(CH$_2$)$_2$OCH$_2$CH$_2$CH$_3$ | 108–110° |
| 4 | H | H | O(CH$_2$)$_2$OCH$_2$CH(CH$_3$)$_2$ | 111–113° |
| 5 | H | H | O(CH$_2$)$_2$OCH$_2$-cyclopentyl | 114–115° |
| 6 | H | H | O(CH$_2$)$_2$OCH$_2$CH$_2$-C$_6$H$_4$-F | 92–94° |
| 7 | H | H | O(CH$_2$)$_2$OCH$_2$-C$_6$H$_4$-F | 107–108° |
| 8 | CN | H | O(CH$_2$)$_2$OCH$_2$CH$_2$CH$_3$ | 104–107° |

EXAMPLE 9

(S)-1-(4-(2-propoxyethoxy)phenoxy)-3((R,S)-2-(tetrahydropyran-4-ylcarbonylamino)-1-methylethylamino)-2-propanol 3 g of (S)-1-(2,3-epoxypropoxy)-4-(2-propoxyethoxy)benzene is added to 2 g N-((R,S)-2-amino-1-methylethyl)tetrahydropyran-4-carboxamide at room temperature and warmed to 50° and kept for 14 hours with stirring. The product is purified over silica gel with methylene chloride/methanol (95:5) (methylene chloride with 10% NH$_3$) as eluent. The title compound is obtained (M.P. 82°–86°—from ether/hexane; $[\alpha]_D^{20} = -0.55°$ (c=1.9/methanol)).

The amine starting material is obtained by reaction of 1,2-diaminopropane and tetrahydropyran-4-carboxylic acid ethyl ester without a solvent at 90°, followed by two chromatographic purifications on silica gel using
 (a) acetone/ethylacetate/conc. NH$_3$ (5:5:0.5) and
 (b) methylene chloride/methanol (7:3) (methylene chloride containing 10% NH$_3$)
One obtains N-((R,S)-2-amino-1-methylethyl)tetrahydropyran-4-carboxamide as an oil.

The epoxide starting material is obtained as follows:
(a) Hydroquinone monobenzyl ether is reacted with 2-bromoethyl-n-propyl ether in aqueous sodium hydroxide and then purified over silica gel with toluene as eluent. The middle fraction gives 1-benzyloxy-4-(2-propoxy-ethoxy)benzene (used without further purification).

(b) The ether obtained under (a) is hydrogenated over 10% palladium on activated charcoal giving as an oil 4-(2-propoxyethoxy)phenol.

(c) The phenol obtained under (b) is reacted in the absence of a solvent and in the presence of a catalytic amount of piperidine with (−)-(2,3-epoxypropoxy)-methylbenzene at 120°. After purification by chromatography (+)-1-(3-benzyloxy-2-hydroxypropoxy)-4-(2-propoxyethoxy)benzene is obtained; [oil; $[\alpha]_D^{20} = +3.2°$ (c=1.5/methanol)].

(d) The ether obtained under (c) is hydrogenated with 10% Palladium over activated charcoal giving (+)-1-(2,3-dihydroxypropoxy)-4-(2-propoxyethoxy)benzene; [oil; $[\alpha]_D^{20} = +4.5$ (c=1.9/methanol)].

(e) The diol obtained under (d) is reacted with p-toluene sulfonyl chloride in pyridine giving (−)-1-(3-toluylsulfonyloxy-2-hydroxypropoxy)-4-(2-propoxyethoxy)benzene [oil; $[\alpha]_D^{20} = -5.3°$ (c=1.9/methanol)].

(f) The tosylate obtained under (c) is converted to (+)-1-(2,3-epoxypropoxy)-4-(2-propoxyethoxy)-benzene with sodium methoxide [oil; $[\alpha]_D^{20} = +6.6°$ (c=2.1/methanol)].

Likewise from step (c) (−)-(2,3-epoxypropoxy)methylbenzene is obtained by reaction of (+)-3-benzyloxy-1,2-propandiol-1-tosylate in methanol at 0°–3° with sodium methoxide (oil; $[\alpha]_D^{20} = -10.8°$, c=1.8/methanol).

EXAMPLE 10

(S)-1-(4-(2-propoxyethoxy)phenoxy)-((R)-2-(tetrahydropyran-4-ylcarbonylamino)-1-methylethylamino)-2-propanol This compound is obtained as for Example 9 except that N-((R)-2-amino-1-methylethyl)tetrahydropyran-4-carboxamide is used instead of the racemate.

The amine reactant is obtained from t-butoxycarbonyl-(D)-alaninamide which is dehydrated with p-toluolsulfonyl chloride in pyridine at 50° for 4 hours to give (R)-2-tert-butoxy-carbonylamino propionitrile which is then reduced with Raney-nickel in ethanol (20% saturated with NH$_3$) to give (R)-2-tert-butoxycarbonyl amino propylamine. Reaction with tetrahydropyran-4-carboxylic acid ethyl ester gives N-((R)-2-tert-butoxycarbonylamino-1-methylethyl)-tetrahydropyran-4-carboxamide. The protecting group is removed with trifluoroacetic acid in ethanol at room temperature giving N-((R)-2-amino-1-methylethyl)-tetrahydropyran-4-carboxamide.

EXAMPLE 11

(S)-1-(4-(2-propoxyethoxy)phenoxy)-3-((S)-2-(tetrahydropyran-4-yl-carbonylamino)-1-methylethylamino)-2-propanol This compound is obtained as for Example 9 except that N-[(S)-2-amino-1-methylethyl]tetrahydropyran-4-carboxamide is used instead of the racemate.

The amine reactant is obtained as for Example 10 from t-butoxycarbonyl-(L)-alaninamide instead of t-butoxycarbonyl-(D)-alaninamide. The following intermediates are obtained:
—(S)-2-tert-butoxycarbonylaminopropionitrile
—(S)-2-tert-butoxycarbonylaminopropylamine
—N-[(S)-2-tert-butoxycarbonylamino-1-methylethyl]-tetrahydropyran-4-carboxamide —N[(S)-2-amino-1-methylethyl]tetrahydropyran-4-carboxamide

EXAMPLE 12

(RS)-1-(4-(2-(propoxyethoxy)phenoxy)-3-((RS)-2-(tetrahydropyran-4-ylcarbonylamino)-1-methylethylamino)-2-propanol This compound is obtained as for Example 9 except that (RS)-1-(2,3-epoxypropoxy)-4-(2-propoxyethoxy)benzene is used instead of the (S)-form.

EXAMPLE 13

(RS)-1-(4-(2-propoxyethoxy)phenoxy)-3-((S)-2-(tetrahydropyran-4-ylcarbonylamino)-1-methylethylamino)-2-propanol This compound is obtained as for Example 11 except that the (RS) epoxide of Example 12 is used instead of the (S)-form.

EXAMPLE 14

(RS)-1-(4-2-propoxyethoxy)phenoxy)-3-((R)-2-(tetrahydropyran-4-ylcarbonylamino)-1-methylethylamino)-2-propanol This compound is obtained as for Example 10 except that the (RS) epoxide of Example 12 is used instead of the (S)-form.

From the appropriate compounds of Formula III wherein $R_x$ is

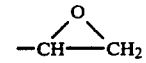

and the appropriate compound of Formula IV the following compounds numbered 15 to 32 of Formula I may be obtained in analogous manner to Examples 9 to 14:

| Example No. | Configuration at carbon substituted by OH | $R_5$ | $R_1$ | $R_5$ | R | M.P (as base) |
|---|---|---|---|---|---|---|
| 15 | (R, S) | (R) | H | $CH_3$ | $O(CH_2)_2$—$OCH_2$—⬠ | 93–95°<br>$[\alpha]_D^{20} = -5, 88°$<br>(c = 1, 3/methanol) |
| 16 | (R, S) | (R, S) | H | $CH_3$ | $O(CH_2)_2$—$OCH_2$—⬠ | — |
| 17 | (R, S) | (S) | H | $CH_3$ | $O(CH_2)_2$—$OCH_2$—⬠ | — |
| 18 | (S) | (R) | H | $CH_3$ | $O(CH_2)_2$—$OCH_2$—⬠ | — |
| 19 | (S) | (S) | H | $CH_3$ | $O(CH_2)_2$—$OCH_2$—⬠ | — |
| 20 | (S) | (R, S) | H | $CH_3$ | $O(CH_2)_2$—$OCH_2$—⬠ | — |
| 21 | (R, S) | (R) | H | $CH_3$ | $O(CH_2)_2OCH_2CH(CH_3)_2$ | 84–86°<br>$[\alpha]_D^{20} = 6, 18°$<br>(c = 1, 6/methanol) |
| 22 | (R, S) | (R, S) | H | $CH_3$ | $O(CH_2)_2OCH_2CH(CH_3)_2$ | — |
| 23 | (R, S) | (S) | H | $CH_3$ | $O(CH_2)_2OCH_2CH(CH_3)_2$ | — |
| 24 | (S) | (R) | H | $CH_3$ | $O(CH_2)_2OCH_2CH(CH_3)_2$ | — |
| 25 | (S) | (S) | H | $CH_3$ | $O(CH_2)_2OCH_2CH(CH_3)_2$ | — |
| 26 | (S) | (R, S) | H | $CH_3$ | $O(CH_2)_2OCH_2CH(CH_3)_2$ | — |
| 27 | (R, S) | (R) | H | $CH_3$ | $O(CH_2)_2OCH_2CH_2$—⌬—F | — |

-continued

| Example No. | Configuration at carbon substituted by OH | Configuration at carbon substituted by $R_5$ | $R_1$ | $R_5$ | R | M.P. (as base) |
|---|---|---|---|---|---|---|
| 28 | (R, S) | (R, S) | H | $CH_3$ | $O(CH_2)_2OCH_2CH_2$—⟨phenyl⟩—F | — |
| 29 | (R, S) | (S) | H | $CH_3$ | $O(CH_2)_2OCH_2CH_2$—⟨phenyl⟩—F | — |
| 30 | (S) | (R) | H | $CH_3$ | $O(CH_2)_2OCH_2CH_2$—⟨phenyl⟩—F | — |
| 31 | (S) | (S) | H | $CH_3$ | $O(CH_2)_2OCH_2CH_2$—⟨phenyl⟩—F | — |
| 32 | (S) | (R, S) | H | $CH_3$ | $O(CH_2)_2OCH_2CH_2$—⟨phenyl⟩—F | — |

EXAMPLE 33

1-(2-fluoro-4-hydroxyphenoxy)-3-[2-(tetrahydropyran-4-ylcarbonylamino)ethylamino]-2-propanol (a) 4.0 g of 4-benzyloxy-2-fluorophenol is reacted with 10 g epichlorhydrin and 0.2 ml piperidine for 90 minutes at 100°. After removal of the volatile material, 40 ml tetrahydrofuran and 20 ml 2M NaOH is added. After 1 hour stirring the solvent is evaporated and the residue partitioned between methylenechloride and water. The organic phase is purified over silica gel with toluene giving 4-benzyloxy-1-(2,3-epoxypropoxy)-2-fluorobenzene (colourless oil).

(b) 4.0 g of epoxide product obtained under (a) is refluxed for 4 hours with 3.1 g N-(2-aminoethyl)tetrahydropyran-4-carboxamide in 50 ml methanol. After removal of solvent the product is chromatographed over silica gel with methylene chloride/ethanol/ammonia 35% in water (90:9:1) giving (late fraction) 1-(4-benzyloxy-2-fluorophenoxy)-3-[2-tetrahydropyran-4-yl-carbonylamino)ethylamino]-2-propanol (M.P. 136°-138°).

(c) 3.75 g of product obtained under (b) is dissolved in 250 ml methanol and reduced with 10% palladium on charcoal at room temperature giving the title compound (M.P. 101°-104°—from ethanol/ether).

The compounds of the invention in free form or as the physiologically acceptable salt possess unique pharmacological activity and can be used as therapeutic agents in man.

In particular, the compounds possess beta adrenoceptor blocking activity as indicated by standard tests, for example, in the spontaneously beating guinea pig atrium (A. Bertholet et al., Postgraduate Medical Journal, 57, Suppl. 1, 9-17, 1981) they inhibit the positive chronotropic isoproterenol effect at bath concentrations from about $10^{-9}$ to $10^{-8}$M.

Thus, in the test above, the compounds have the following potencies expressed as a dose which doubles the concentration of isoproterenol needed to elicit a 50% increase in heart rate (i.e. $ID_{50}$).

| Example No. | Guinea Pig Atrium Effective Molar Dose, M. ($ID_{50}$) |
|---|---|
| 1 | $1.2 \times 10^{-7}$ |
| 2 | $5 \times 10^{-8}$ |
| 3 | $8 \times 10^{-8}$ |
| 4 | $5 \times 10^{-8}$ |
| 5 | $3 \times 10^{-8}$ |
| 6 | $2 \times 10^{-8}$ |
| 7 | $2 \times 10^{-7}$ |
| 8 | $7 \times 10^{-8}$ |
| 9 | $4 \times 10^{-8}$ |
| 10 | $3 \times 10^{-8}$ |
| 11 | $1.6 \times 10^{-7}$ |
| 15 | $3 \times 10^{-8}$ |
| 21 | $7 \times 10^{-8}$ |
| Propranolol | $3 \times 10^{-9}$ |
| Atenolol | $2 \times 10^{-7}$ |
| Metoprolol | $1.2 \times 10^{-8}$ |

The beta adrenoceptor blocking activity in the heart can also be demonstrated in a whole animal model. For example, inhibition of isoproterenol induced tachycardia in the pithed rat show in vivo potencies many times higher than expected from their potencies in the guinea pig atria model and most of the potencies are comparable or higher than propranolol.

Thus, in the test above the following compounds exhibit effective beta-1 adrenoceptor blocking activity at the doses indicated below.

| Example No. | Pithed Rat Effective Dose (ID$_{50}$) (ug/kg) |
| --- | --- |
| 1 | 100 |
| 2 | 20 |
| 3 | 15 |
| 4 | 20 |
| 5 | 30 |
| 6 | 30 |
| 7 | 20 |
| 8 | 20 |
| 9 | 3 |
| 10 | 0.6 |
| 11 | 20 |
| 15 | 10 |
| 21 | 5 |
| Propranolol | 20 |
| Atenolol | 30 |
| Metoprolol | 20 |

The compounds are particularly useful as beta adrenoceptor blocking agents and can therefore be used for the prophylaxis and therapy of diseases which are commonly known to respond to blockade of beta adrenoceptors such as those found in the heart. An example of such diseases are hypertension, angina pectoris, thyrotoxicosis, migraine and for the disturbances of the heart such as supraventricular tachycardia.

In addition the compounds have more marked and wider spread beneficial pharmacological properties then would be expected for compounds having this type of structure. In particular their activity is much more cardioselective than presently known from similar compounds.

The can be demonstrated in vitro in tracheal preparations of the guinea pig which are prepared according to standard procedures in which a portion of the tracheal muscle is allowed to relax under the influence of isoproterenol and in the presence of known concentrations of the compound to be tested.

In the test above potency in tracheal preparations is much less than in the atria as determined above. In the case of Examples, 2, 3, 4, 5, 6, 10 and 15 no blocking effect of the responses to isoproterenol are found in the trachea at concentrations as high as $3 \times 10^{-5}$ mol/l, and are therefore considered to have virtually absolute selectivity or are specific for the cardiac beta 1 adrenoceptor. By comparison propranolol exerts a blocking effect in this model at a concentration of $1 \times 10^{-8}$ mol/l. The selectivities of commonly known selective beta adrenoceptor blockers such as metoprolol and atenolol are, in this model, 5 and 20 respectively.

Thus the selectivity of these compounds is very much higher than standard drugs commonly available.

In the pithed rat preparation the compounds can produce a 100% inhibition of the effects of isoproterenol administered in the dose of 0.1 ug/kg i.v. on heart rate but have no effect on the blood pressure response to isoproterenol at doses as high as 3 mg/kg i.v.

In the conscious dog the maximum inhibitory effect of all compounds on the isoproterenol induced tachycardia at a dose of isoproterenol of 0.1 ug/kg i.v. is from 40-60% of that obtainable with non selective agents such as propranolol. The lack of complete blockade in the dog reflects the significant number of beta-2 cardiac adrenoceptors in this preparation which are not blocked by highly cardioselective compounds. The high or absolute selectivity of these compounds is of major importance in the treatment of hypertension where exacerbation of an asthmatic condition may be precipitated by currently commercially available compounds.

The compounds with a bridging oxygen in the para position to the oxymethylene group also possess a degree of intrinsic sympathomimetic activity, a property which is useful in preventing undue bradycardia and helps to reduce the incidence of heart failure in patients with heart muscle disease. This property can be demonstrated as an increase in resting heart rate in a pithed rat preparation using standard procedures in which the maximum effect of cumulative doses of drug up to 3 mg/kg are observed. Examples 1 to 11,15 and 21 all showed increases in heart rate in this pithed rat preparation and the maximum increases in heart rate ranged from 21-105 beats/min.

In the anaesthetised, vagotomized cat spinalised at the level of second cervical vertebrae the compounds exert an increase in cardiac contractile force at a dose of from about 20 to about 2,500 ug/kg i.v. as measured with a strain gauge arch sewn into the left ventricle. The effect may also be measured as a concentration dependent stimulation of the isolated spontaneously beating guinea pig atrium.

These compounds therefore, possess beta agonist as well as selective beta antagonist properties and are useful as cardiotonics, for example, for the treatment of heart insufficiency, especially in situations where a positive inotropic effect is desired without significant influence on blood pressure. The balance between the agonistic and antagonistic activities is particularly favourable for compounds 9 and 33; the agonist component contributes to the cardiotonic activity whilst the antagonist component protects against an excessive increase in contractile force which may lead to arrhythmias.

Beta blockade is also useful in preventing large increases in heart rate and hence protecting the heart against formation of arrhythmic beats. Thus these compounds are particularly useful for the treatment of disturbances of the heart rhythmn such as supraventricular tachycardia.

These compounds also show the added advantage of lowering intraocular pressure when instilled as a buffered solution to the cornea of eyes. Thus, these compounds can therefore be used for the treatment of glaucoma. This property can be demonstrated using a standard test in rabbits. Reductions in intraocular pressure are observed by as much as 4 mm Hg over a two hour period.

The compounds are therefore useful as beta-1 adrenoceptor blocking agents, for example, for the prophylaxis and therapy of coronary artery diseases such as angina pectoris, conditions which are associated with sympathetic over stimulation, for example nervous heart complaints, myocardial infarction, hypertension, for the immediate treatment of migraine and for the treatment of glaucoma and thyrotoxicosis. In view of the antiarrhythmic effect they are useful as antiarrhythmics for the treatment of disturbances in the heart rhythmn such as supraventricular tachycardia.

For these uses described above, the dose will vary according to the substance used, the mode of administration and the desired treatment. In general however the dose required to treat hypertension and related coronary heart diseases with an oral formulation are obtained with a daily dosage of 0.5 to 5 mg/kg body weight; administration may be effected in one, two or three divided doses or as a sustained release form. For larger mammals such as man the total daily dosage of these compounds is from about 10 to 500 mg; suitable pharmaceutical formulations for oral administration generally contain from 2.5 to 250 mg of the compounds together with solid or liquid carriers and/or diluents known to persons skilled in the art.

For the treatment of glaucoma the dose is usually administered as sterile eye drops as a 0.5 to 2% solution in a buffer containing boric acid.

The compounds have more marked and wider spread beneficial pharmacological properties that would be expected from compounds having this type of structure. In particular, the compounds are characterised by being virtually cardiospecific which is not present in similar known compounds.

Of the compounds of the invention in optically active form in which the carbon atom in the 2 position of the 3-aminopropoxy side chain has the S-configuration are more pharmacologically active than the corresponding R enantiomer.

The preferred uses of the compound are against coronary heart diseases and for hypertension.

The compounds of the invention in free form or in the form of the pharmaceutically acceptable salts may be administered alone or in suitable dosage forms. The present invention also provides for a pharmaceutical composition comprising a compound of the invention, in free form or in salt form, probably an acid addition salt form, in association with a pharmaceutical carrier or diluent. Such forms, for example, a solution or a tablet, may be produced according to known methods.

We claim:

1. A method of effecting beta adrenoceptor blockade which comprises administering to a human in need of such treatment a therapeutically effective amount of a compound of Formula I,

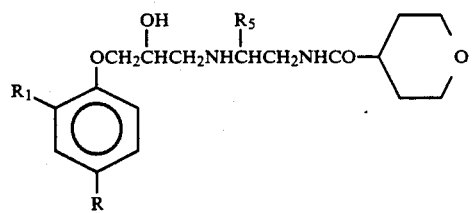

wherein
A) R is O(CH$_2$)$_2$—O—R$_3$ and
   (a) R$_1$ and R$_5$ are hydrogen and R$_3$ is n-propyl, isobutyl, cyclopentylmethyl, benzyl or 2-(p-fluorophenyl)ethyl;
   (b) R$_1$ is fluorine and R$_5$ is hydrogen and R$_3$ is n-propyl;
   (c) R$_1$ is methyl and R$_5$ is hydrogen and R$_3$ is cyclopropylmethyl;
   (d) R$_1$ is cyano and R$_5$ is hydrogen and R$_3$ is n-propyl;
   (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen, or a physiologically hydrolysable ester thereof,
in free form or in a pharmaceutically acceptable salt form.

2. A method of treating conditions associated with sympathetic overstimulation which comprises administering a therapeutically effective amount of a compound of Formula I,

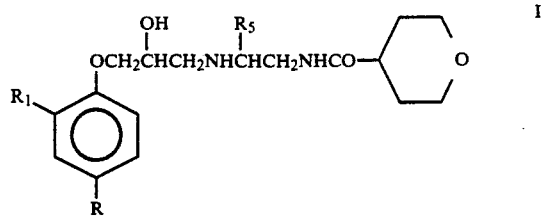

wherein
A) R is O(CH$_2$)$_2$—O—R$_3$ and
   (a) R$_1$ and R$_5$ are hydrogen and R$_3$ is n-propyl, isobutyl, cyclopentylmethyl, benzyl or 2-(p-fluorophenyl)ethyl;
   (b) R$_1$ is fluorine and R$_5$ is hydrogen and R$_3$ is n-propyl;
   (c) R$_1$ is methyl and R$_5$ is hydrogen and R$_3$ is cyclopropylmethyl;
   (d) R$_1$ is cyano and R$_5$ is hydrogen and R$_3$ is n-propyl;
   (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen, or a physiologically hydrolysable ester thereof,
in free form or in a pharmaceutically acceptable salt form.

3. A method of treating hypertension which comprises administering a therapeutically effective amount of a compound of Formula I,

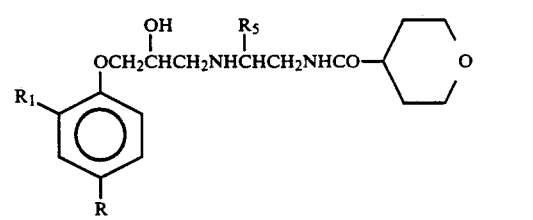

wherein
A) R is O(CH$_2$)$_2$—O—R$_3$ and
   (a) R$_1$ and R$_5$ are hydrogen and R$_3$ is n-propyl, isobutyl, cyclopentylmethyl, benzyl or 2-(p-fluorophenyl)ethyl;
   (b) R$_1$ is fluorine and R$_5$ is hydrogen and R$_3$ is n-propyl;
   (c) R$_1$ is methyl and R$_5$ is hydrogen and R$_3$ is cyclopropylmethyl;
   (d) R$_1$ is cyano and R$_5$ is hydrogen and R$_3$ is n-propyl;
   (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen, or a physiologically hydrolysable ester thereof,
in free form or in a pharmaceutically acceptable salt form.

4. A method of treating migraine which comprises administering a therapeutically effective amount of a compound of Formula I,

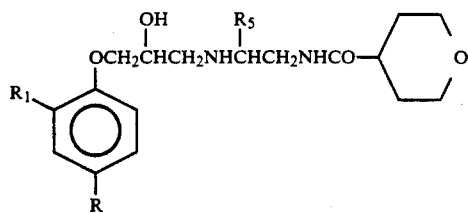

wherein
A) R is O(CH$_2$)$_2$—O—R$_3$ and
  (a) R$_1$ and R$_5$ are hydrogen and R$_3$ is n-propyl, isobutyl, cyclopentylmethyl, benzyl or 2-(p-fluorophenyl)ethyl;
  (b) R$_1$ is fluorine and R$_5$ is hydrogen and R$_3$ is n-propyl;
  (c) R$_1$ is methyl and R$_5$ is hydrogen and R$_3$ is cyclopropylmethyl;
  (d) R$_1$ is cyano and R$_5$ is hydrogen and R$_3$ is n-propyl;
  (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen, or a physiologically hydrolysable ester thereof,
in free form or in a pharmaceutically acceptable salt form.

5. A method of treating glaucoma which comprises administering a therapeutically effective amount of a compound of Formula I,

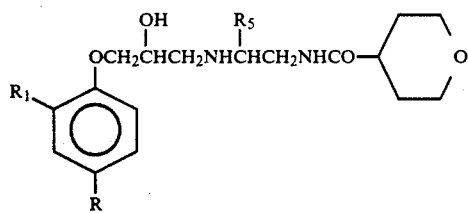

wherein
A) R is O(CH$_2$)$_2$—O—R$_3$ and
  (a) R$_1$ and R$_5$ are hydrogen and R$_3$ is n-propyl, isobutyl, cyclopentylmethyl, benzyl or 2-(p-fluorophenyl)ethyl;
  (b) R$_1$ is fluorine and R$_5$ is hydrogen and R$_3$ is n-propyl;
  (c) R$_1$ is methyl and R$_5$ is hydrogen and R$_3$ is cyclopropylmethyl;
  (d) R$_1$ is cyano and R$_5$ is hydrogen and R$_3$ is n-propyl;
  (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen, or a physiologically hydrolysable ester thereof,
in free form or in a pharmaceutically acceptable salt form.

6. A method of treating thyrotoxicosis which comprises administering a therapeutically effective amount of a compound of Formula I,

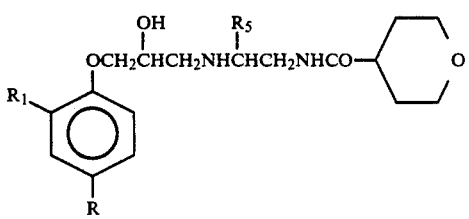

wherein
A) R is O(CH$_2$)$_2$—O—R$_3$ and
  (a) R$_1$ and R$_5$ are hydrogen and R$_3$ is n-propyl, isobutyl, cyclopentylmethyl, benzyl or 2-(p-fluorophenyl)ethyl;
  (b) R$_1$ is fluorine and R$_5$ is hydrogen and R$_3$ is n-propyl;
  (c) R$_1$ is methyl and R$_5$ is hydrogen and R$_3$ is cyclopropylmethyl;
  (d) R$_1$ is cyano and R$_5$ is hydrogen and R$_3$ is n-propyl;
  (e) R$_1$ is hydrogen, R$_5$ is methyl and R$_3$ is alkyl of 2 to 5 carbon atoms, cycloalkylmethyl of 5 to 7 carbon atoms in the cycloalkyl part thereof or —(CH$_2$)$_n$—R' wherein n is 0, 1 or 2 and R' is phenyl or monofluorophenyl; or
B) R is hydroxy, R$_1$ is fluorine and R$_5$ is hydrogen, or a physiologically hydrolysable ester thereof,
in free form or in a pharmaceutically acceptable salt form.

* * * * *